United States Patent [19]

Wolf et al.

[11] 4,402,950

[45] Sep. 6, 1983

[54] PROCESS AND PREPARATION FOR DEACTIVATING VIRUSES

[75] Inventors: Erich Wolf, Overath; Andreas Lembke, Eutin-Sielbeck; Rolf Deininger, Cologne, all of Fed. Rep. of Germany

[73] Assignee: Chimicasa GmbH, Chur, Switzerland

[21] Appl. No.: 184,135

[22] Filed: Sep. 4, 1980

Related U.S. Application Data

[63] Continuation of Ser. No. 5,764, Jan. 23, 1979, abandoned.

[30] Foreign Application Priority Data

Jan. 27, 1978 [LU] Luxembourg ........................... 78955

[51] Int. Cl.³ ............................................ A01N 65/00
[52] U.S. Cl. .................................................... 424/195
[58] Field of Search ......................................... 424/195

[56] References Cited

U.S. PATENT DOCUMENTS 3,595,975  7/1971  Gauvreau ........................... 424/263

OTHER PUBLICATIONS

Chemical Abstracts 59:14406 (a) (1963).

*Primary Examiner*—Jerome D. Goldberg
*Attorney, Agent, or Firm*—Kontler, Grimes & Battersby

[57] ABSTRACT

The invention relates to a process and a preparation for deactivating viruses inside living human and animal organisms by application of a terpene obtainable from aromatic plants by steam distillation. The terpenes cited are: black pepper oil, cinnamon flower oil, cardamon oil, linallyl acetate, cinnamic aldehyde, safrol, carvon and cis/trans citral.

13 Claims, No Drawings

PROCESS AND PREPARATION FOR DEACTIVATING VIRUSES

This is a continuation, of application Ser. No. 005,764, filed Jan. 23, 1979, now abandoned.

The invention relates to a process and a preparation for deactivating viruses inside living human and animal organisms. During use thereof, cell damage and other harmful side effects in the organisms should be prevented.

The process according to the invention is characterised by the use of a terpene obtainable by steam distillation from aromatic plants, in a daily dose of 5 to 500 mg (milligrams), preferably 25 to 100 mg per 50 kg (kilograms) of the weight of the living organism.

These terpenes demonstrate a viricidal activity (i.e. a damaging effect on viruses) in a concentration which is one or more powers of ten lower than the concentration at which these terpenes have toxic effects on living cells. This wide range gives a degree of play in tolerance which is advantageous from the dosage point of view and thus makes it possible to administer these terpenes safely in veterinary and human medicine.

Since these terpenes can be obtained from aromatic plants which have been used for feeding animals and humans for many years and have proved harmless in the doses in question, it is also to be expected that the quantities of terpenes to be used according to the invention will not cause any serious, harmful side effects.

Terpenes or mixtures of terpenes which have proved suitable are those consisting of black pepper oil, cinnamon flower oil, cardamom oil, linallyl acetate, cinnamic aldehyde, safrol, carvon and cis/trans citral, used individually or mixed together.

A pharmaceutical preparation according to the invention, i.e. for deactivating viruses inside living human and animal organisms, is prepared by obtaining one or more of these terpenes by steam distillation from the parts of the aromatic plants where the relevant terpenes are contained and then mixing them into a pharmaceutical carrier substance in a ratio of 1:100 to 20:100.

A pharmaceutical preparation according to the invention, i.e. for deactivating viruses inside living human and animal organisms, consists of one or more of the terpenes listed, mixed into a pharmaceutical carrier substance in a ratio of 1:100 to 20:100.

The terpenes used can be obtained from aromatic plants by steam distillation as follows:

back pepper oil from the peppercorns of *Piper nigrum;*
cinnamon flower oil from the flowers of *Cinnamonum cassia;*
cardamom oil from the seeds of *Elettaria cardamomum;*
linallyl acetate from the flowers of Lavandula;
cinnamic aldehyde from the bark of *Cinnamonum ceylanicum;*
safrol from the root of Sassafras;
carvon from the fruit of *Carum carvi,* and
cis/trans citral from the leaves of *Cymbopogon citratus.*

Instead of these natural terpenes, identical synthetic terpenes may be used, if available. However, natural terpenes obtained from aromatic plants are preferred.

The activity obtained according to the invention is demonstrated by comparison tests as follows.

Cell cultures were cultivated in various culture vessels under optimal culture conditions from permanent strains of the types "Girardi Heart" (GH), "Flow 12000" (FL), "Intestine 407" (IN) and "Vero Kidney" (VR), so that a layer of cell culture containing about 0.25 mg of cell substance formed on the bottom of the vessels.

A suspension of virus particles of the Adeno Type 6 virus was also added.

For the total of eight terpenes listed in Table I, twenty cell cultures of each type of cell were prepared. The twenty cell cultures of each type of cell were treated with differing amounts of the relevant terpene in the following manner.

The first two cell cultures were given $10^5$ mg of terpene per 10 kg of cell substance. The next two cell cultures were given $10^4$ mg of terpene based on 10 kg of cell substance. The next two cell cultures were given $10^3$ mg of terpene based on 10 kg of cell substance and so on to the last two of these twenty cell cultures, which were given 0.1 mg of terpene per 10 kg of cell substance. Thus, in each case, two similar cell cultures were treated with the same amount of the same terpene. For control purposes, one of these two identical cell cultures was left as it was, whilst the other was inoculated with $5 \times 10^6$ virus particles per 0.25 mg of cell substance, in addition to the virus suspension used. The same procedure was also followed with the other cell cultures and terpenes.

The cell cultures thus treated were left to stand and observed after four days and six days. This observation was carried out by microscopic investigation of the cell culture for cell damage. The damage observed was divided into four stages, as follows:

| | | |
|---|---|---|
| Stage 0 | means | no damage |
| Stage 1 | means | slackened growth of the cell formations |
| Stage 2 | means | the cells become spherical and detach themselves from the bottom |
| Stage 3 | means | the cell structures are substantially or totally destroyed. |

It was found that the inoculated cell cultures which were protected with a very small amount of terpene reached stage 3 or 2, as the viruses had damaged the cells. The inoculated cell cultures containing a very large amount of terpene also reached stage 3 or 2, as the cells were damaged by the excessive terpene. However, the inoculated cell cultures containing only a moderate amount of terpene were at stage 0, i.e. undamaged. Thus, the moderate amount of terpene damaged the viruses sufficiently and protected the cells from viral attack, without the cells being damaged directly by the terpene. The terpene concentrations with which stage 0 and, in some isolated cases, stage 1 were observed in the inoculated cell cultures after four and six days result in sufficient damage to the viruses without damaging the cells, and are given in Table I.

Column 1 of Table I gives the terpene used, the second column gives the treated cell strain, abbreviated as hereinbefore, and the third column gives the amount of terpene used in mg, based on 10 kg of treated cell substance, for the range of concentrations in which no appreciable cell damage (i.e. stage 0) was observed. This range is the therapeutic range which in each case extends over several powers of ten. Thus, for all the terpenes listed in the Table, the desired viricidal activity occurs at a concentration which is several powers of ten lower than the lowest concentration at which cell damage was observed, i.e. at which the microorganisms to be protected could be damaged.

TABLE I

| Terpene | treated cell substance | range of viricidal concentration at which no cell damage was observed, in mg of terpene per 10 kg of treated cell substance |
|---|---|---|
| black pepper oil | GH | $10^3$ to 0.1 |
| (Oleum Piperis nigri) | FL | 100 to 0.1 |
| | IN | 100 to 1 |
| | VE | 100 to 0.1 |
| Cinnamon flower oil | GH | $10^3$ to 0.1 |
| (Oleum Cassiae flores) | FL | $10^3$ to 0.1 |
| | IN | 100 to 0.1 |
| | VE | 100 to 0.1 |
| Cardamom oil | GH | 100 to 1 |
| (Oleum Cardamomi) | FL | 100 to 1 |
| | IN | 100 to 1 |
| | VE | 100 to 10 |
| Linallyl acetate | GH | 100 to 0.1 |
| | FL | 100 to 1 |
| | IN | 100 to 1 |
| | VE | 100 to 1 |
| cinnamic aldehyde | GH | 100 to 1 |
| | FL | 100 to 1 |
| | IN | 100 to 1 |
| | VE | 100 to 1 |
| safrol | GH | 100 to 1 |
| | FL | 100 to 1 |
| | IN | 100 to 10 |
| | VE | 100 to 1 |
| carvon | GH | 100 to 1 |
| | FL | 100 to 1 |
| | IN | 100 to 1 |
| | VE | 100 to 1 |
| cis/trans citral | GH | 10 to 1 |
| | FL | 10 to 1 |
| | IN | 100 to 1 |
| | VE | 100 to 1 |

EXAMPLE 1 (Injection solution)

50 g of black pepper oil are dissolved in 2 l (liters) of 1,2-propanediol. The solution is sterilised in the autoclave for 50 minutes at 121° C. (Celsius), then cooled and poured into ampoules in 2 g amounts.

An ampoule contains 50 mg of black pepper oil and contains an average daily dose for an adult weighing 70 kg, for the therapy and prophylaxis of influenza infections. For human and animal patients of other weights, the daily dose must be modified accordingly in proportion to the patient's weight.

The mixing ratio of terpene to 1,2-propanediol in this example is 2.5:100; other mixing ratios for injection solutions are possible, within the range 1:100 to 5:100, but the daily dose of the injection solution must then be adjusted to the different terpene content of the injection solution.

EXAMPLE 2 (Aerosol)

325 g of black pepper oil are dissolved in 631.8 g of ether mixed with 1,805.07 g of ethanol. To this solution are added 31.6 g of ester of castor oil fatty acids with ethoxylated glycerol and 210.6 g of capryl/capric acid triglyceride. 2.68 g of this mixture, together with 2.527 g of difluorodichloromethane as the propellant, are packed in a spray can with a capacity of 20 cc (cubic centimeters). The spray can is sealed and comprises a metering valve which releases a specific amount of mixture each time it is actuated, and this mixture is then vaporised as an aerosol under the pressure of the difluorodichloromethane.

Corresponding adjustment and dimensions of the metering valve ensure that, on each application, a single dose containing 6.5 mg of black papper oil is released.

For the treatment and prevention of influenza infections, the aerosol is sprayed into the mouth or nose and inhaled. A suitable treatment for an adult weighing 70 kg is eight such single doses per day, containing a total of $8 \times 6.5 = 50$ mg of black pepper oil.

The aerosol can also be used to treat areas of the skin affected by virus infections, in which case an area of 50 $cm^2$ (square centimeters) is sprayed with seven spray doses each containing 6.5 mg of black pepper oil.

The mixing ratio of terpene to the aerosol substance is 12:100 in this example; other mixing ratios for the aerosol are possible, in the range from 5:100 to 20:100, but then the daily dose must be adjusted to the modified terpene content of each spray portion.

EXAMPLE 3 (Capsules)

A capsule filling is prepared from a mixture of 12.5 g of black pepper oil and 12.5 g of cinnamon flower oil and 3 g of soya lecithin as the emulsifier. Each capsule contains 28 mg of this filling and is sealed with a capsule shell consisting of 87.5 mg of gelatine and 37.5 mg of glycerol.

For the treatment and prevention of influenza infections, one to four capsules per day are administered orally to an adult patient weighing 70 kg; if more than one capsule is taken, they are spread out over the day.

One capsule contains 25 mg of terpene; however, variations are possible, with a capsule containing from 10 to 50 mg of terpene, but then the daily dose must be adjusted to the modified terpene content.

EXAMPLE 4 (Stick)

1 g of black pepper oil is mixed into a stable carrier composition. The carrier composition consists of 59.84 g of Vaseline album and 39.16 g of paraffin and is thoroughly mixed with the terpene at 70° C. and then poured into a mould to form a stick and hardened by cooling.

For local use, the stick is rubbed on to the skin and distributed so that 1 ml (milliliter) of stick compound—which contains 5 mg of terpene in this example—is distributed over 50 $cm^2$ of skin. This can be repeated 3 times daily.

The mixing ratio of terpene to carrier composition is 1:100 in this example; other mixing ratios are possible, in the range from 1:100 to 5:100.

EXAMPLE 5 (Ointment)

3.2 g of Paraffinum durum and 86.8 g of white Vaseline are heated to 60° C. and stirred. 10 g of cinnamon flower oil are mixed into the warm mixture. The mixture is cooled and can be used as an ointment for local application. About 0.1 ml of ointment—containing about 5 mg of terpene—are spread over 50 $cm^2$ of skin. This can be repeated 8 times a day.

The mixing ratio of terpene to the mixture of Paraffinum durum and white Vaseline is 11:100 in this example, but other mixing ratios for the ointment are also possible, within the range from 5:100 to 20:100.

EXAMPLE 6 (Plaster)

A vapour-proof plaster film is produced from textile material made vapour-proof by coating with plastics on the underside. On the other side (the contact side) the plaster is coated with a plaster compound in a layer 1 mm (millimeter) thick. To prepare the plaster compound, 97 g of lead plaster, 9 g of yellow wax, 9 g of dammar, 10 g of colophony and 1 g of turpentine are mixed together, heated to 100° C. and stirred until the molten compound is no longer foaming. Then 5 g of black pepper oil are mixed in and the plaster compound is then applied to the contact side of the plaster film and hardened by cooling.

The plaster is placed with its contact side next to the skin and left for four hours. It can then be replaced by a new plaster.

The mixing ratio of terpene to plaster compound is 4:100 in this example; however, other mixing ratios are also possible within the range from 1:100 to 10:100.

Using the preparations and treatments given in the examples, viral attacks can be prevented or stopped without causing any cell damage in the treated organism or any other serious side effects.

The examples given are open to modification by using, instead of the terpene mentioned, the same amount of another terpene from Table I or a mixture of several of these terpenes. In all these cases, the viricidal activity can be obtained without having to take into account any undesirable side effects.

I claim:

1. A process for deactivating viruses inside living human and animal organisms infected with said viruses comprising administering to one of said organisms a terpene selected from the group consisting of black pepper oil, cinnamon flower oil, cardamon oil, linallyl acetate, cinnamic aldehyde, carvon, and cis/trans citral, in a dosage amount effective to deactivate said viruses but ineffective to cause toxic effects on living cells of the living organism.

2. The process according to claim 1, characterized in that said terpene is mixed with a pharmaceutical carrier substance in a mixing ratio of from 1:100 to 2:100.

3. The process according to claim 1, characterized in that said terpene is administered by injection to said organism and further characterized in that said terpene is dissolved in 1,2 propanediol in a mixing ratio of 1:100 to 5:100.

4. A process according to claim 1 wherein the amount of terpene administered is a dosage amount having at its maximum concentration, in milligrams of terpene per 50 kilograms of the weight of the living organism, a concentration which is at least one power of 10 lower than the lowest concentration at which the terpene exhibits toxic effects on living cells of the living organism.

5. A process according to claim 1 or 4 wherein the dosage amount is a daily dose of from 5 to 500 mg per 50 kg of the weight of the living organism.

6. A process for deactivating viruses inside living human and animal organisms infected with said viruses comprising administering to said organism a terpene selected from the group consisting of black pepper oil, cinnamon flower oil, cardamon oil, linallyl acetate, cinnamic aldehyde, carvon, cis/trans citral and combinations thereof, in a daily dose of from 5 to 500 mg per 50 kg of the weight of the living organism.

7. A process according to claim 5 or 6 wherein the dose is within the range of from 25 to 100 mg.

8. The process according to claim 1, wherein said terpene is dissolved in 1,2 propanediol in a mixing ratio of about 2.5:100.

9. The process according to claim 1 wherein said terpene is black pepper oil.

10. An injectable pharmaceutical preparation for deactivating viruses inside living human and animal organisms infected with said viruses, said preparation including a terpene selected from the group consisting of black pepper oil, cinnamon flower oil, cardamon oil, linallyl acetate, carvon, and cinnamic aldehyde and 1,2 propanediol as a carrier substance in a mixing ratio of from 1:100 to 20:100 said terpene being included in a dosage amount effective to deactivate said viruses but ineffective to cause a toxic effect on the living cells of the organisms.

11. The preparation according to claim 10 characterized in that said at least one terpene is black pepper oil.

12. The preparation according to claim 10 adapted to be administered to said organisms by injection and characterized in that said at least one terpene is dissolved in 1,2 propanediol in a mixing ratio of 1:100 to 5:100.

13. The preparation according to claim 12 characterized in that said mixing ratio is about 2.5:100.

* * * * *